(12) United States Patent
Gribble et al.

(10) Patent No.: US 8,981,144 B2
(45) Date of Patent: Mar. 17, 2015

(54) METHOD FOR SYNTHESIZING 2-CYANO-3,12-DIOXOOLEAN-1, 9(11)-DIEN-28-OIC ACID METHYL ESTER AND DERIVATIVES THEREOF

(75) Inventors: Gordon W. Gribble, Lebanon, NH (US); Liangfeng Fu, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 353 days.

(21) Appl. No.: 13/466,502

(22) Filed: May 8, 2012

(65) Prior Publication Data

US 2013/0303797 A1 Nov. 14, 2013

(51) Int. Cl.
*C07C 69/75* (2006.01)
*C07J 75/00* (2006.01)

(52) U.S. Cl.
CPC ........................................ *C07J 75/00* (2013.01)
USPC ......................................................... 560/128

(58) Field of Classification Search
CPC ................................. C07J 75/00; C07J 63/008
USPC ......................................................... 560/128
See application file for complete search history.

(56) References Cited

U.S. PATENT DOCUMENTS

| | | | |
|---|---|---|---|
| 6,326,507 B1 | 12/2001 | Gribble et al. | 558/415 |
| 6,552,075 B2 | 4/2003 | Gribble et al. | 514/522 |
| 6,974,801 B2 | 12/2005 | Honda et al. | 514/25 |
| 7,288,568 B2 | 10/2007 | Gribble et al. | 514/519 |
| 7,863,327 B2 | 1/2011 | Gribble et al. | 514/521 |
| 7,915,402 B2 | 3/2011 | Anderson et al. | 540/519 |
| 7,943,778 B2 | 5/2011 | Jiang et al. | 548/247 |
| 8,034,955 B2 | 10/2011 | Gribble et al. | 548/241 |
| 2008/0233195 A1 | 9/2008 | Spoorn et al. | 424/486 |
| 2009/0048204 A1 | 2/2009 | Walling et al. | 514/49 |
| 2009/0060873 A1 | 3/2009 | Sporn et al. | 424/85.6 |
| 2009/0326063 A1 | 12/2009 | Sporn et al. | 514/529 |
| 2010/0048887 A1 | 2/2010 | Anderson et al. | 540/8 |
| 2010/0048892 A1 | 2/2010 | Anderson et al. | 544/154 |
| 2010/0048911 A1 | 2/2010 | Jiang et al. | 548/250 |
| 2011/0245206 A1 | 10/2011 | Jiang et al. | 514/112 |
| 2011/0245233 A1 | 10/2011 | Anderson et al. | 514/212.04 |

FOREIGN PATENT DOCUMENTS

| | | |
|---|---|---|
| AL | WO 2008/136838 A1 | 11/2008 |
| WO | WO 2004/064723 A2 | 8/2004 |
| WO | WO 2005/046732 A2 | 5/2005 |
| WO | WO 2008/064132 A2 | 5/2008 |
| WO | WO 2009/023232 A1 | 2/2009 |
| WO | WO 2010/093944 A2 | 8/2010 |

OTHER PUBLICATIONS

Rao et al. "Chemical Modifications of Natural Triterpenes—Glycyrrhetinic and Boswellic Acids: Evaluation of their Biological Activity" Tetrahedron 2008 64(51):11541-11548.

*Primary Examiner* — Barbara P Badio
(74) *Attorney, Agent, or Firm* — Licata & Tyrrell P.C.

(57) ABSTRACT

The present invention is a method for preparing triterpenoids such as 2-cyano-3,12-dioxoolean-1,9-dien-28-methyl ester and derivatives thereof from oleanic acid, ursolic acid, betulinic acid, sumaresinolic acid or hederagenin.

12 Claims, No Drawings

METHOD FOR SYNTHESIZING 2-CYANO-3,12-DIOXOOLEAN-1, 9(11)-DIEN-28-OIC ACID METHYL ESTER AND DERIVATIVES THEREOF

BACKGROUND OF THE INVENTION

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn & Roberts (1986) *J. Clin. Invest.* 78:329-332; Ohshima & Bartsch (1994) *Mutat. Res.* 305:253-264). The enzymes that mediate the constitutive synthesis of nitric oxide and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada, et al. (1991) *Pharmacol. Rev.* 43:109-142; Nathan & Xie (1994) *Cell* 78:915-918; Siebert & Masferrer (1994) *Receptor* 4(1):17-23; Tamir & Tannebaum (1996) *Biochim. Biophys. Acta* 1288:F31-F36). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang, et al. (1994) *Cancer Res.* 54:701-708; Nishino, et al. (1988) *Cancer Res.* 48:5210-5215). However, the biological activity of these naturally occurring molecules is relatively weak, and therefore the synthesis of new analogs to enhance their potency has been undertaken (see, e.g., Honda, et al. (1997) *Bioorg. Med. Chem. Lett.* 7:1623-1628; Honda, et al. (1998) *Bioorg Med Chem Lett.* 8(19):2711-2714).

In this respect, U.S. Pat. No. 6,326,507, U.S. Pat. No. 6,552,075, U.S. Pat. No. 7,288,568, U.S. Pat. No. 7,863,327, U.S. Pat. No. 8,034,955, US 2009/0060873, US 2009/0048204, WO 2008/136838 and WO 2009/023232 teach the use of 2-cyano-3,12-dioxooleana-1,9(11)-dien-28-oic acid (CDDO), and derivatives thereof such as 2-cyano-3,12-dioxoolean-1,9(11)-dien-28-oic acid methyl ester (CDDO-Me) and amide derivatives, for the treatment of diseases such as cancer, Alzheimer's disease, Parkinson's disease, inflammatory bowel diseases, and multiple sclerosis. Similarly, U.S. Pat. No. 6,974,801 and WO 2004/064723 teach the use of 2-cyano-3,12-dioxooleana-1,9(11)-dien-28-onitrile (CNDDO), 1-(2-cyano-3,12-dioxooleana-1,9(11)-dien-28-oyl)imidazole (CDDO-Im), 1-(2-cyano-3,12-dioxooleana-1,9(11)-dien-28-oyl)-2-methylimidazole, and 1-(2-cyano-3,12-dioxooleana-1,9(11)-dien-28-oyl)-4-methylimidazole in the prevention or treatment of cancer, Alzheimer's disease, Parkinson's disease, multiple sclerosis, rheumatoid arthritis, and other inflammatory diseases. Furthermore, the use of triterpenoids such as CDDO, CDDO-Me, CDDO-Im, and CDDO-Ethylamide in stimulating the growth and repair of bone and cartilage (US 2008/0233195 and WO 2008/064132) as well as in inhibiting HIV-1 replication (WO 2005/046732) has been described. US 2009/0326063 further teaches the use of synthetic triterpenoids in the prevention and treatment of renal/kidney disease, insulin resistance/diabetes, fatty liver disease, and/or endothelial dysfunction/cardiovascular disease.

Combination therapies of CDDO or CDDO-Me and a chemotherapeutic agent, immunosuppressive agent, or proteasome inhibitor are described in U.S. Pat. No. 7,435,755, U.S. Pat. No. 7,795,305, US 2009/0018146, US 2009/0048205, WO 2002/047611 and WO 2009/023845 for the treatment of cancer and graft versus host disease. Moreover, formulations for improved oral bioavailability of CDDO-Me are disclosed in WO 2010/093944.

Given the activity of CDDO and CDDO-Me, additional oleanolic acid derivatives have been developed for use in treating cancer, cardiovascular disease, neurodegenerative disease, renal/kidney disease, diabetes, arthritis and inflammatory conditions such as obesity, hypertension, atherosclerosis, coronary heart disease, stroke, peripheral vascular disease, hypertension, nephropathy, neuropathy, myonecrosis, ulcerative colitis, Crohn's disease, irritable bowel syndrome, retinopathy and metabolic syndrome. See U.S. Pat. No. 7,915,402, U.S. Pat. No. 7,943,778, US 2010/0048887, US 2010/0048892, US 2010/0048911, US 2011/0245206 and US 2011/0245233.

In view of the therapeutic activities of this class of triterpenoids, it would be advantageous to have an improved method of prepared these compounds. Desired improvements include one or more of reducing the number of synthetic steps, improving the yield and reducing the cost of synthesis.

SUMMARY OF THE INVENTION

The present invention is a method for preparing a triterpenoid compound by (a) methylating the carboxylic acid group of a compound of Formula I to afford a methyl ester; (b) oxidizing the hydroxyl group of the methyl ester of Formula I and forming a double bond in Ring A to form an enone; (c) epoxidating Ring C of the enone to form an epoxide; and (d) forming a C-ring enol and halogenating the A-ring enone to yield a compound of Formula II.

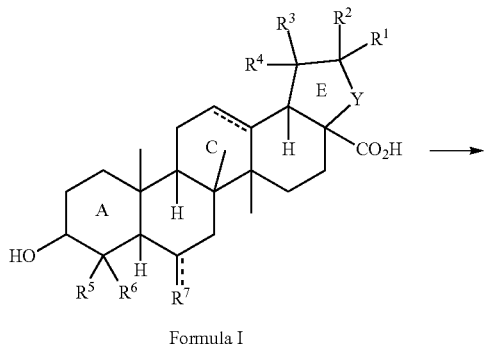

Formula I

-continued

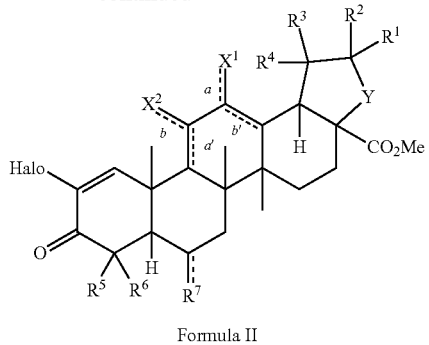

Formula II

In some embodiments, the compound of Formula I is oleanolic acid, ursolic acid, betulinic acid, sumaresinolic acid or hederagenin, or a derivative thereof. In other embodiments, step (a) employs an electrophilic methyl source, step (b) uses an iodine oxidizing agent, step (c) includes the use of a peroxyacid and/or step (d) employs a hydrogen halide and diatomic halogen molecule. In other embodiments, the method further includes one or more of contacting a compound of Formula II with a cyanide ion source; aminating the compound of Formula II, e.g., via Buchwald-Hartwig amination; or coupling or cross-coupling an alkyl, alkenyl, alkynyl or aryl group to a compound of Formula II, e.g., via a Sonogashira, Suzuki, Stifle, or Negishi reaction. In a specific embodiment, the instant method is used in the preparation of CDDO-Me.

DETAILED DESCRIPTION OF THE INVENTION

An improved method for preparing triterpenoids, including CDDO-Me and derivatives thereof, from natural compounds has now been developed. Derivatives with comparable or improved activities compared to CDDO or CDDO-Me can now be synthesized at lower cost, in improved yield and/or in less time. The CDDO-Me derivatives synthesized herein can be used in the treatment of disease, especially inflammatory diseases.

The instant method of synthesizing triterpenoids includes the steps of (a) methylating the carboxylic acid group of a compound of Formula I to afford a methyl ester; (b) oxidizing the hydroxyl group of the methyl ester of Formula I and forming a double bond in Ring A to form an enone; (c) epoxidating Ring C of the enone to form the epoxide; and (d) forming a C-ring enol and halogenating the A-ring enone to yield a compound of Formula II (Scheme 1).

SCHEME 1

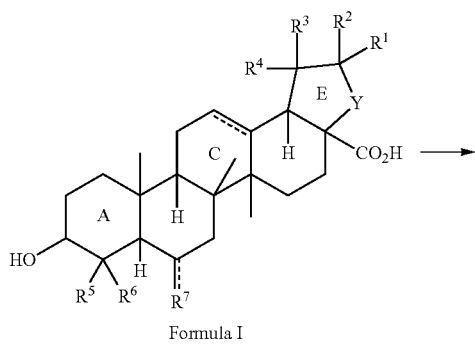

Formula I

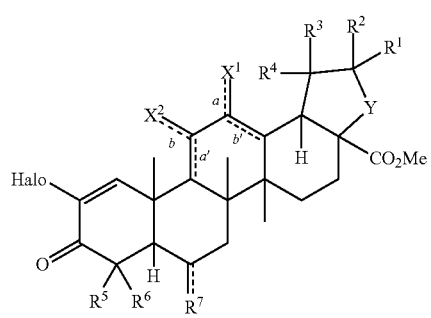

Formula II

As more particularly outlined in Scheme 2, the step of methylating the carboxylic acid group of a compound of Formula I is carried out by contacting a compound of Formula I with a methylating agent. In accordance with this step of the method, the methylating agent is an electrophilic methyl source including, but not limited to iodomethane, dimethyl sulfate, dimethyl carbonate, diazomethane, or with methylating reagents such as methyl triflate or methyl fluorosulfonate, optionally in the presence of a base such as $K_2CO_3$ or $Li_2CO_3$. In a particular embodiment, the compound of Formula I is methylated with iodomethane.

The resulting methyl ester (e.g., Formula Ia; Scheme 2) is then contacted with an oxidizing agent to oxidize the hydroxyl group and form a double bond in Ring A. In accordance with certain embodiments, the oxidizing agent is an iodine oxidizing agent such as o-iodoxybenzoic acid (IBX) (Nicolaou, et al. (2002) *J. Am. Chem. Soc.* 124:2245-2258), diacetoxyiodobenzene (DAIB), fluorous DAIB (F-DAIB), Dess-Martin-Periodinane (DMP), or a stabilized formulation of IBX (SIBX; Ozanne, et al. (2003) *Org. Lett.* 5:2903). In particular embodiments, the methyl ester of Formula I is oxidized with IBX in one or a combination of suitable solvents such as DMSO and phenyl fluoride (fluorobenzene).

In a further embodiment, the step of epoxidating Ring C of the enone (e.g., Formula Ib; Scheme 2) includes the use of an oxidant, in particular a peroxyacid such as meta-chloroperoxybenzoic acid (mCPBA), peroxyacetic acid, or potassium peroxymonosulfate (Oxone). Acid-catalyzed opening of the epoxide and halogenation (e.g., bromination) of the A Ring is achieved with a hydrogen halide such as (HBr or HI) and a diatomic halogen molecule such as $Br_2$ or $I_2$ (Scheme 2). In particular embodiments, a compound of Formula Ib is contacted with a peroxyacid to form a Ring C epoxide and the resulting intermediate is reacted with a hydrogen halide and diatomic halogen molecule to form the C-ring enol and halogenate the A-ring.

SCHEME 2
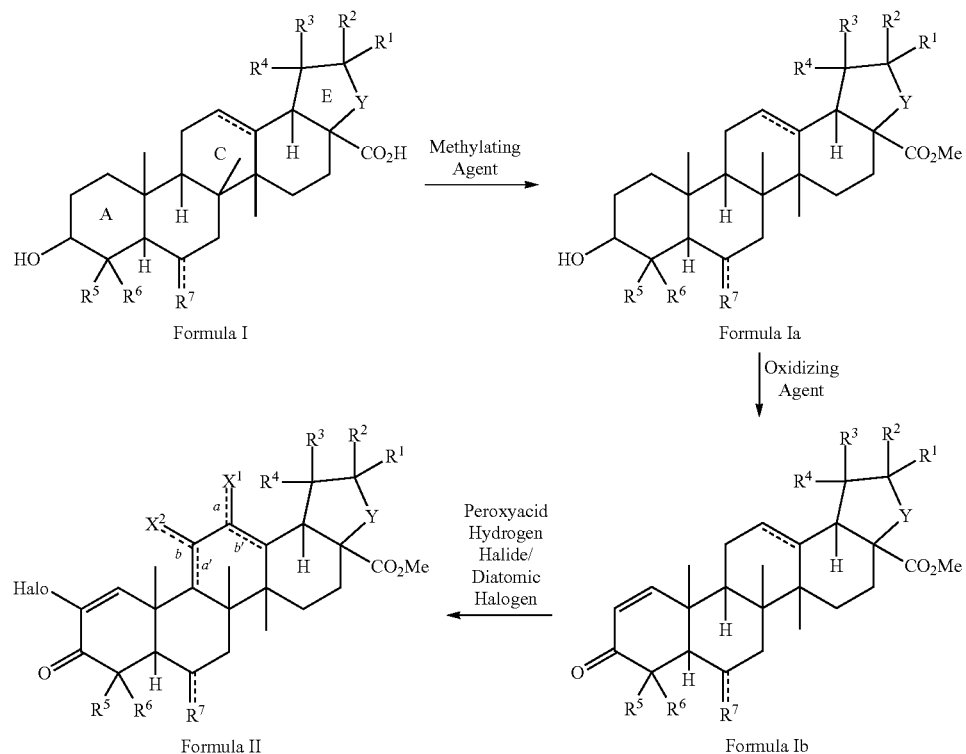
As used in the context of the present invention, Formula I includes naturally occurring starting materials such as oleanolic acid, ursolic acid, betulinic acid, sumaresinolic acid or hederagenin, or derivatives thereof.
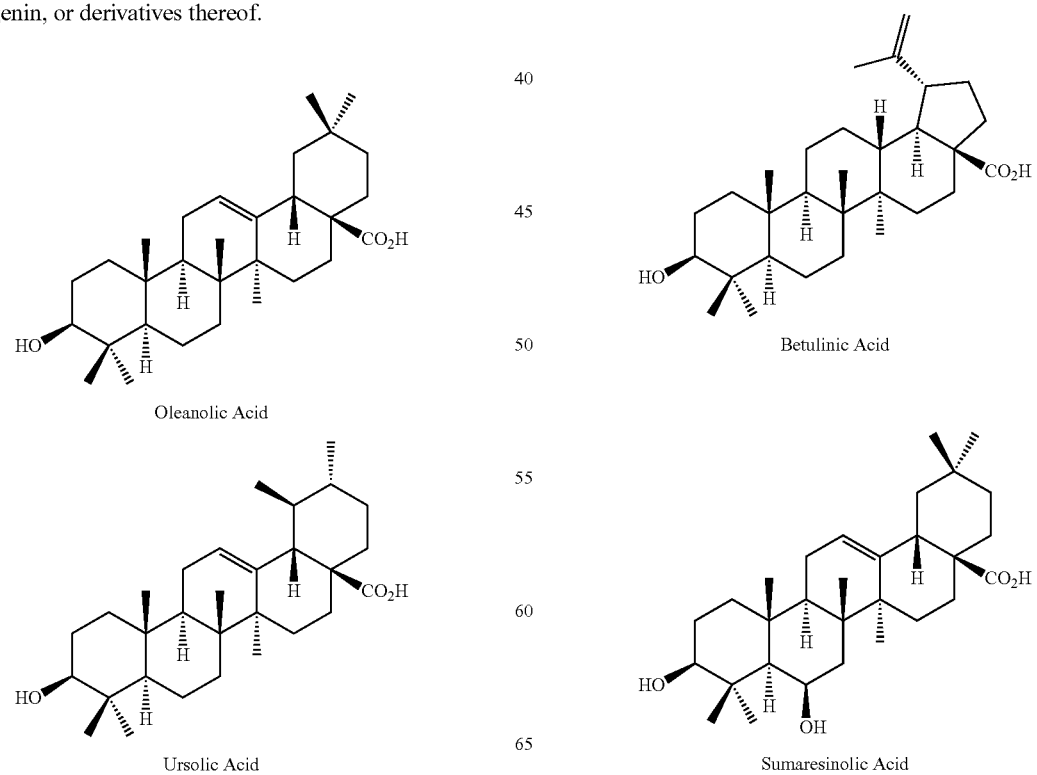

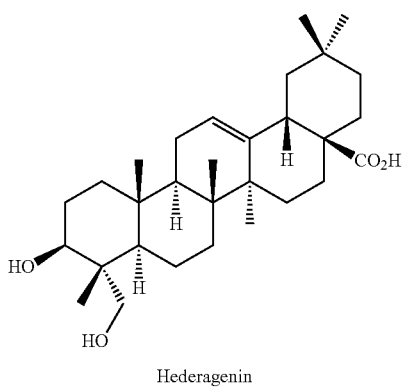

Hederagenin

In this respect, with reference to the Formula I, Ia, Ib, and II:

$X^1$ is oxygen, dashed bonds a and a' are present, $X^2$ is hydrogen and dashed bonds b and b' are absent, or $X^2$ is oxygen, dashed bonds b and b' are present, $X^1$ is hydrogen and dashed bonds a and a' are absent;

Y is —$CH_2$— or —$CH_2$—$CH_2$—;

$R^1$, $R^2$, $R^3$ and $R^4$ are each independently a hydrogen, hydroxyl, alkyl, substituted alkyl, alkenyl, alkoxy or substituted alkoxy group;

$R^5$ and $R^6$ are each independently hydrogen, halo, alkyl, alkenyl, alkynyl, aryl, aralkyl, heteroaryl, heteroaralkyl, acyl, alkoxy, aryloxy, aralkoxy, heteroaryloxy, heteroaralkoxy, acyloxy, alkylamino, dialkyl-amino, arylamino, aralkylamino, hetero-arylamino, heteroaralkylamino, amido, or a substituted version of any of these groups, or $R^5$ and $R^6$ are taken together and are alkanediyl, alkenediyl, arenediyl, alkoxydiyl, alkenyloxydiyl, alkylaminodiyl, alkenylaminodiyl, or alkenylaminooxydiyl; and $R^7$ is hydrogen, hydroxy or oxo.

In accordance with this invention, Formula II serves as a substrate for the synthesis of CDDO-Me and derivatives thereof. In one embodiment, a compound of Formula II is contacted with a cyanide ion source such as $K_4[Fe(CN)_6]$, KCN, NaCN, ZnCN, CuCN, $(CH_3)_2C$(—OH)CN or TMSCN to displace the A ring halide with a cyanide ion. In particular embodiments, the cyanide ion is CuCN. In accordance with this embodiment, CDDO-Me is produced. A complete synthesis of CDDO-Me from oleanolic acid is provided in Scheme 3.

SCHEME 3

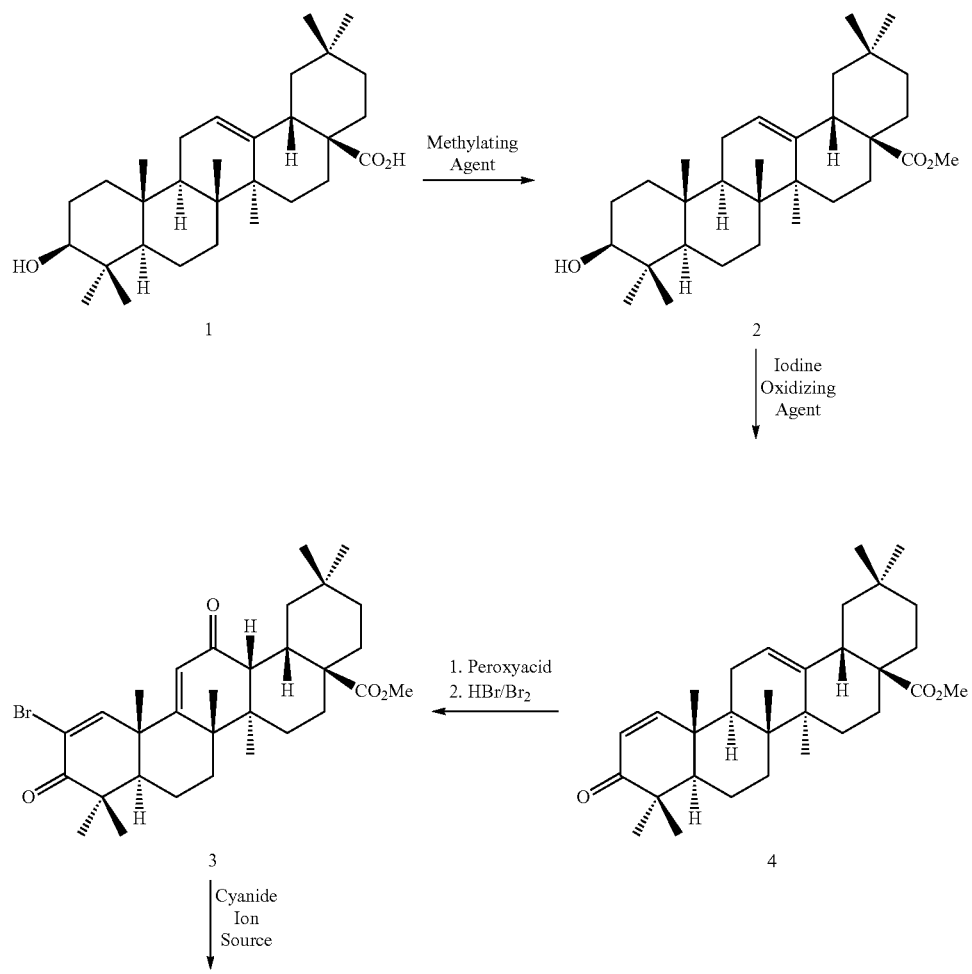

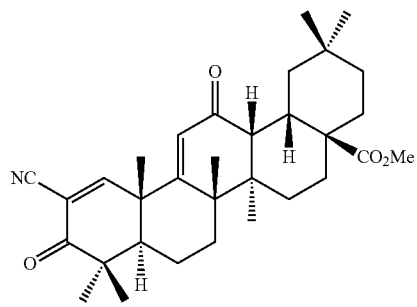

5

In other embodiments, the compound of Formula II can be reacted with a variety of reagents to replace the highly reactive halogen on Ring A. In particular, the halo group can be replaced with, for example, a moiety selected from the group consisting of cyano, hydroxy, amino, fluoroalkyl, alkenyl, alkynyl, aryl, heteroaryl, alkoxy, aryloxy, acyloxy, alkylamino, arylamino, amido, or a substituted version of any of these groups, or —C(=O)$R^a$, wherein $R^a$ is hydrogen, hydroxy, halo, amino, hydroxyamino, amido or mercapto; or alkyl, alkenyl, alkynyl, aryl, aralkyl, heteroaryl, heteroaralkyl, alkoxy, alkenyl-oxy, alkynyloxy, aryloxy, aralkoxy, heteroaryloxy, heteroaralkoxy, acyloxy, alkylamino, dialkylamino, alkoxyamino, alkenylamino, alkynylamino, arylamino, aralkylamino, heteroarylamino, heteroaralkyl-amino, alkylsulfonylamino, amido, alkylsilyloxy, and substituted versions of any of these groups.

For example, the compound of Formula II can be aminated or coupled or cross-coupled with an alkyl, alkenyl, alkynyl or aryl group to provide a variety of substituents on Ring A. For example, certain compounds of Formula II can be aminated via Buchwald-Hartwig amination (Buchwald & Muci (2002) *Top. Curr. Chem.* 219:133-209; Hartwig (1999) *Pure Appl. Chem.* 71:1417; Buchwald & Yang (1999) *J. Orgmet. Chem.* 576:125; Hartwig (1998) *ACIEE* 37:2046; Hartwig (1998) *Acc. Chem. Res.* 31:852; Buchwald et al. (1998) *Acc. Chem. Res.* 31:805) to provide amides and amines 6. Moreover, when 6 is a formamide (i.e., R=H and R'=CHO), isonitrile 7 can be readily synthesized under mild conditions (Porcheddu, et al. (2005) *J. Org. Chem.* 70:2361-3). In addition, Sonogashira coupling (Sonogashira, et al. (1975) *Tetrahedron Lett.* 16:4467-70) provides alkynes 8 and 10. Likewise, Suzuki (Miyuara, et al. (1979) *Tetrahedron Lett.* 20:3437-40; Miyaura & Suzuki (1979) *Chem. Comm.* 19:866-7; Miyaura & Suzuki (1995) *Chem. Rev.* 95:2457-2483), Stille (Kosugi, et al. (1977) *Chem. Lett.* 301; Milstein & Stille (1978) *J. Am. Chem. Soc.* 100:3636), and Negishi (King, et al. (1977) *J. Chem. Soc. Chem. Commun.* 19:683) cross-coupling reactions provide compounds having the structure of compound 9 and dimers such as compounds 10-17 are readily produced when the halogen of Formula II is iodide. Other compounds of Formula II or can also be subjected to these reactions.

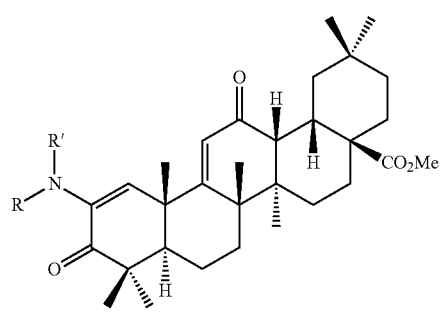

6

(R = H and R' = H or $R^bCO$;
$R^b$ is H, halo, alkyl, aryl, alkenyl,
alkynyl, nitro, amino, or -$CF_3$)

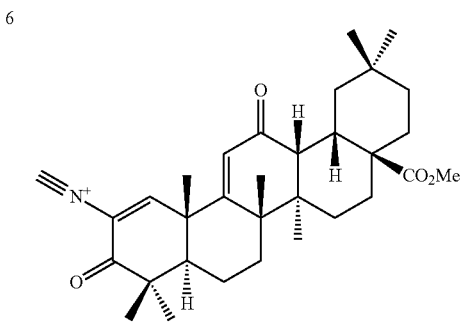

7

-continued
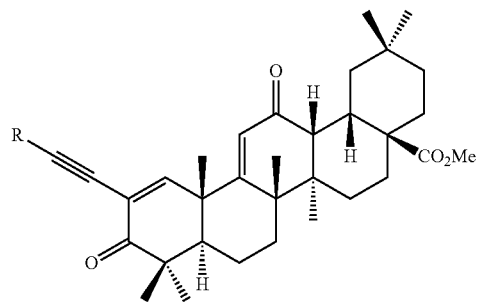
8
(R = alkyl, aryl, alkenyl, alkynyl)
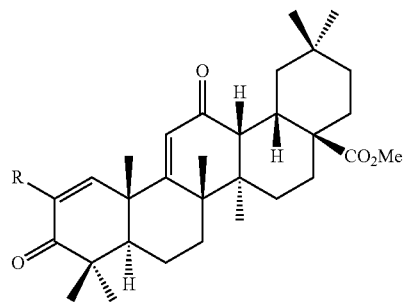
9
(R = alkyl, aryl, alkenyl, alkynyl)
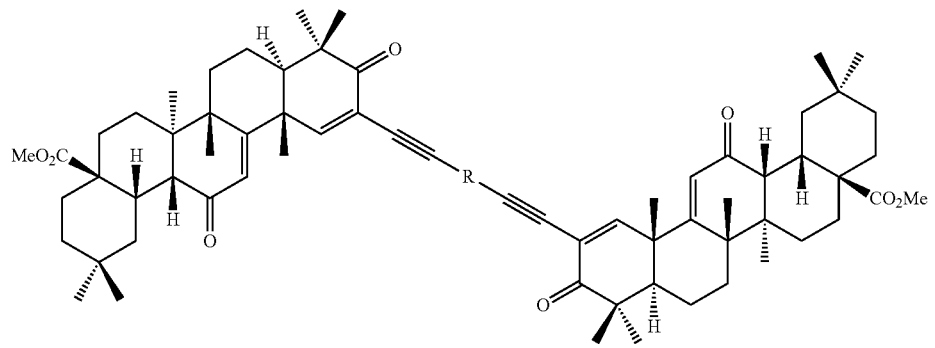
10
(R = alkyl, aryl, alkenyl, alkynyl)
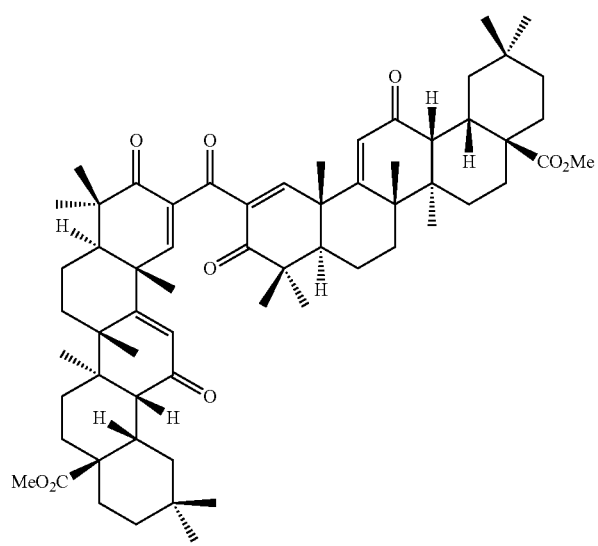
11
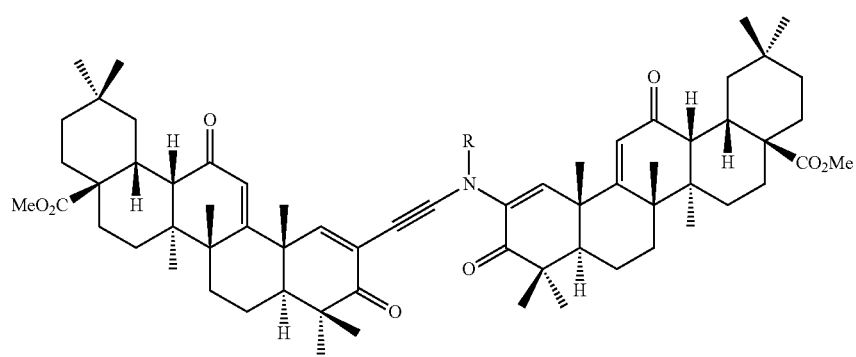
12
(R = H, alkyl, aryl, alkenyl, alkynyl)

-continued
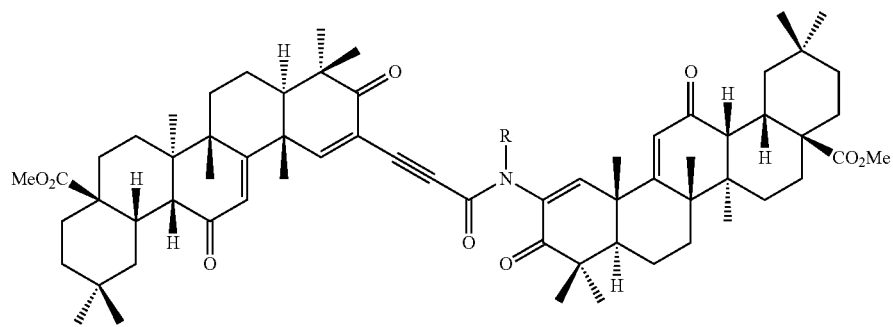
(R = H, alkyl, aryl, alkenyl, alkynyl)
13
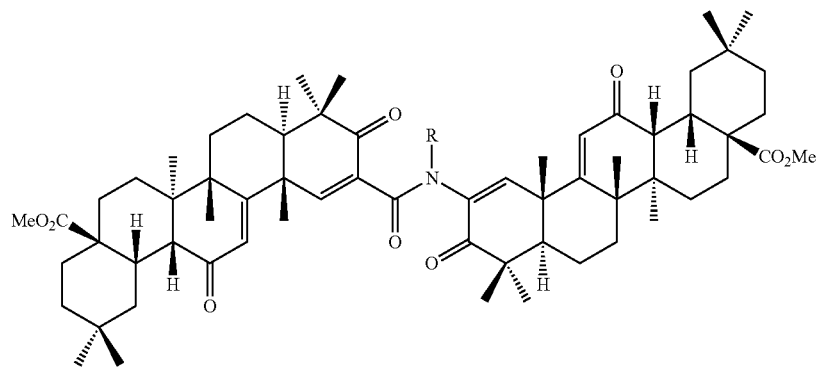
(R = H, alkyl, aryl, alkenyl, alkynyl)
14
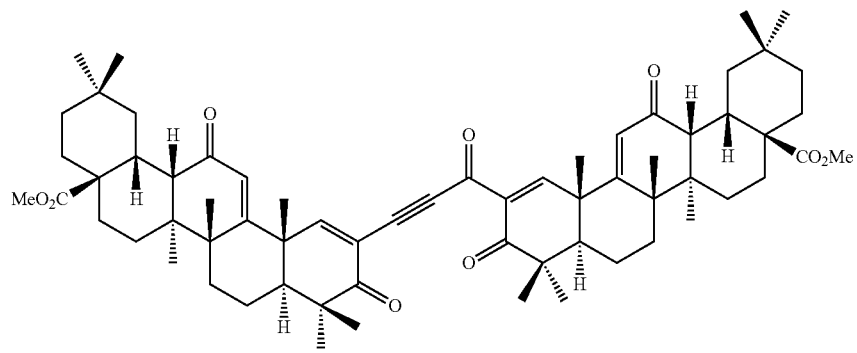
15
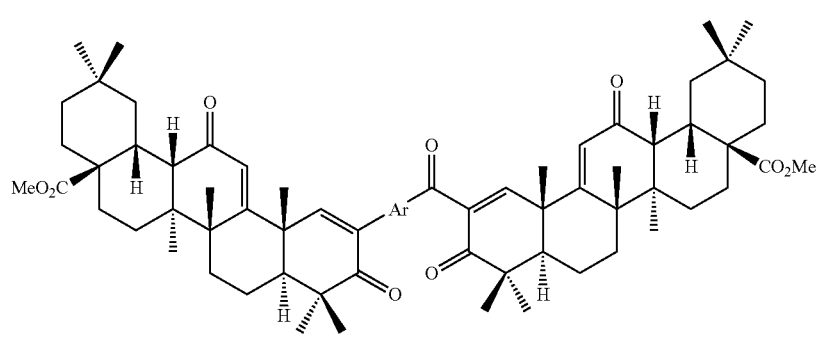
16

-continued

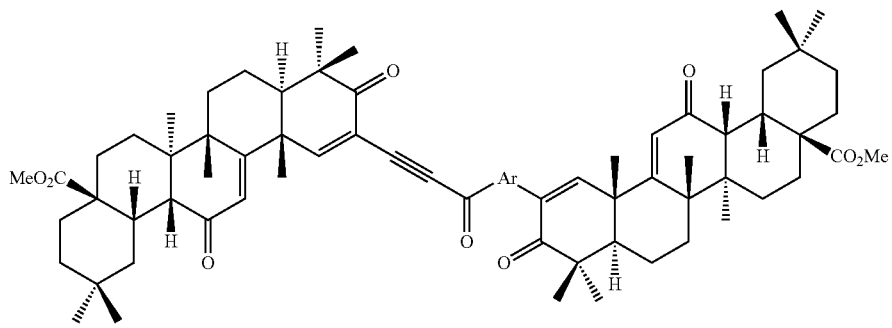

Accordingly, using the method described herein, compounds having the structure of Formula III can be obtained.

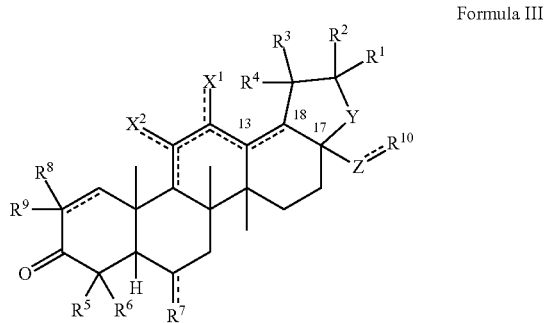

Formula III wherein, $X^1$ and $X^2$ are independently hydrogen, $OR^c$, $NR^cR^d$, or $SR^c$, wherein $R^c$ is a hydrogen, cyano, —$CF_3$, nitro, amino, or substituted or unsubstituted heteroaryl group;

$R^d$ is hydrogen, hydroxyl, alkyl, aryl, aralkyl, acyl, alkoxy, aryloxy, acyloxy, alkylamino, arylamino, amido, or a substituted version of any of these groups;

or a substituent convertible in vivo to hydrogen;

provided that $R^d$ is absent when the atom to which it is bound is part of a double bond, further provided that when $R^d$ is absent the atom to which it is bound is part of a double bond;

Y is —$CH_2$— or —$CH_2$—$CH_2$—;

Z is a covalent bond, —C(=O)—, alkanediyl, alkenediyl, alkynediyl, or a substituted version of any of these groups;

the dashed bonds can be independently present or absent;

$R^1$, $R^2$, $R^3$ and $R^4$ are each independently a hydrogen, hydroxyl, alkyl, substituted alkyl, alkoxy or substituted alkoxy group;

$R^5$ and $R^6$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or $R^5$ and $R^6$ are taken together and are alkanediyl, alkanediyl, arenediyl, alkoxydiyl, alkenyloxydiyl, alkylaminodiyl, alkenylaminodiyl, or alkenylaminooxydiyl;

$R^7$ is hydrogen, hydroxy or oxo;

$R^8$ and $R^9$ are independently hydrogen, hydroxyl, halo, cyano, —C≡$CR^e$, —$CO_2R^e$, —$COR^e$, alkyl, alkenyl, alkynyl, aryl, aralkyl, heteroaryl, heteroaralkyl, acyl, alkoxy, aryloxy, acyloxy, alkylamino, arylamino, nitro, amino, amido, —C(=O)$R^e$ or a substituted version of any of these groups, or $R^8$ and $R^9$ together are oxo, wherein $R^e$ is hydrogen, hydroxy, halo, amino, hydroxyamino, azido or mercapto; or $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-dialkylamino, $C_1$-$C_{15}$-alkoxyamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-alkylsulfonylamino, $C_1$-$C_{15}$-amido, $C_1$-$C_{15}$-alkylsilyloxy, or substituted versions of any of these groups;

$R^{10}$ is a hydrogen, hydroxyl, —$NR^fR^g$, cyano, halo, azido, phosphate, 1,3-dioxoisoindolin-2-yl, mercapto, silyl or —COOH group, substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_1$-$C_{15}$-alkylthio, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_1$-$C_{12}$-alkylsulfinyl, $C_2$-$C_{12}$-alkenylsulfinyl, $C_2$-$C_{12}$-alkynylsulfinyl, $C_6$-$C_{12}$-aryl sulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups, a —$CO_2Me$, carbonyl imidazole, —CO-D-Glu(OAc)$_4$, —$CONH_2$, —$CONHNH_2$, —$CONHCH_2CF_3$, or —C(=O)-heteroaryl group, or Z and $R^{10}$ form a three to seven-membered ring, such that Z and $R^{10}$ are further connected to one another through one or more of —O— and alkanediyl, further wherein Z is —CH— and $R^{10}$ is —CH$_2$— or Z, $R^{10}$, and carbon numbers 13, 17 and 18 form a ring such that $R^{10}$ is bound to carbon 13, wherein Y is methanediyl or substituted methanediyl and $R^{10}$ is —O—, wherein $R^f$ and $R^g$ are independently hydrogen, hydroxyl, alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkoxy, thioacyl, alkylsulfonyl, alkenylsulfonyl, alkynylsulfonyl, arylsulfonyl, aralkylsulfonyl, heteroarylsulfonyl, or heteroaralkylsulfonyl, or a substituted version of any of these groups.

Alternative substituents for $R^1$-$R^{10}$ include those disclosed in any one of U.S. Pat. No. 7,915,402; U.S. Pat. No. 7,943,778; U.S. Pat. No. 8,071,632; U.S. Pat. No. 8,124,656; and U.S. Pat. No. 8,124,799, each of which is incorporated herein by reference in its entirety.

Using a compound of Formula II as a substrate, amides (Formula V), ethers (Formula VI), and esters (Formula VII and Formula VIII) are readily obtained with techniques known in the art. See U.S. Pat. No. 6,974,801 and US 2008/0233195. Accordingly, in some embodiments, the compound synthesized by the invention has the structure as set forth in Formulae V-VIII.

Formula V

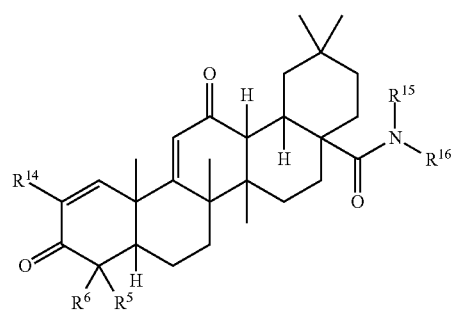

Formula VI

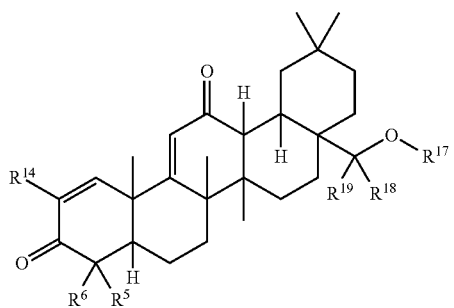

Formula VII

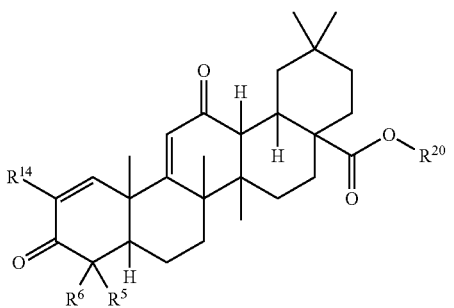

Formula VIII

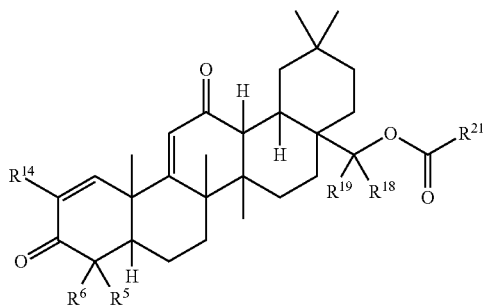

In accordance with Formulae V-VIII, $R^5$ and $R^6$ are as defined for Formula III;

$R^{14}$ is hydrogen, hydroxyl, halo, cyano, alkyl, alkenyl, alkynyl, aryl, aralkyl, heteroaryl, heteroaralkyl, acyl, alkoxy, aryloxy, acyloxy, alkylamino, arylamino, nitro, amino, amido, or a substituted version of any of these groups or —C≡CR$^c$, —CO$_2$R$^c$, —COR$^c$, or —C(=O)R$^e$ as defined above;

$R^{18}$ and $R^{19}$ are independently a hydrogen, hydroxyl, halo, alkyl, nitro or amino group;

$R^{15}$, $R^{16}$, $R^{17}$, $R^{20}$ and $R^{21}$ are independently a hydrogen, hydroxyl, —NR$^f$R$^g$ as defined above, cyano, halo, azido, phosphate, 1,3-dioxoisoindolin-2-yl, mercapto, silyl or —COOH group, substituted or unsubstituted versions of C$_1$-C$_{15}$-alkyl, C$_2$-C$_{15}$-alkenyl, C$_2$-C$_{15}$-alkynyl, C$_6$-C$_{15}$-aryl, C$_7$-C$_{15}$-aralkyl, C$_1$-C$_{15}$-heteroaryl, C$_2$-C$_{15}$-heteroaralkyl, C$_1$-C$_{15}$-acyl, C$_1$-C$_{15}$-alkoxy, C$_2$-C$_{15}$-alkenyloxy, C$_2$-C$_{15}$-alkynyloxy, C$_6$-C$_{15}$-aryloxy, C$_7$-C$_{15}$-aralkyloxy, C$_1$-C$_{15}$-heteroaryloxy, C$_2$-C$_{15}$-heteroaralkyloxy, C$_1$-C$_{15}$-acyloxy, C$_1$-C$_{15}$-alkylamino, C$_2$-C$_{15}$-alkenylamino, C$_2$-C$_{15}$-alkynylamino, C$_6$-C$_{15}$-arylamino, C$_7$-C$_{15}$-aralkylamino, C$_1$-C$_{15}$-heteroarylamino, C$_2$-C$_{15}$-heteroaralkylamino, C$_1$-C$_{15}$-amido, C$_1$-C$_{15}$-alkylthio, C$_2$-C$_{15}$-alkenylthio, C$_2$-C$_{15}$-alkynylthio, C$_6$-C$_{15}$-arylthio, C$_7$-C$_{15}$-aralkylthio, C$_1$-C$_{15}$-heteroarylthio, C$_2$-C$_{15}$-heteroaralkylthio, C$_1$-C$_{15}$-acylthio, C$_1$-C$_{12}$-thioacyl, C$_1$-C$_{12}$-alkylsulfonyl, C$_2$-C$_{12}$-alkenylsulfonyl, C$_2$-C$_{12}$-alkynylsulfonyl, C$_6$-C$_{12}$-arylsulfonyl, C$_7$-C$_{12}$-aralkylsulfonyl, C$_1$-C$_{12}$-heteroarylsulfonyl, C$_1$-C$_{12}$-heteroaralkylsulfonyl, C$_1$-C$_{12}$-alkylsulfinyl, C$_2$-C$_{12}$-alkenylsulfinyl, C$_2$-C$_{12}$-alkynylsulfinyl, C$_6$-C$_{12}$-aryl sulfinyl, C$_7$-C$_{12}$-aralkylsulfinyl, C$_1$-C$_{12}$-heteroarylsulfinyl, C$_1$-C$_{12}$-heteroaralkylsulfinyl, C$_1$-C$_{12}$-alkylphosphonyl, C$_1$-C$_{12}$-alkylphosphate, C$_2$-C$_{12}$-dialkylphosphate, C$_1$-C$_{12}$-alkylammonium, C$_1$-C$_{12}$-alkylsulfonium, C$_1$-C$_{15}$-alkylsilyl, or a substituted version of any of these groups, a —CO$_2$Me, carbonyl imidazole, —CO-D-Glu(OAc)$_4$, —CONH$_2$, —CONHNH$_2$, —CONHCH$_2$CF$_3$, or —C(=O)-heteroaryl group.

In yet other embodiments, a compound of Formula II is used as a substrate in the synthesis of a dimer as represented by the Formula IV:

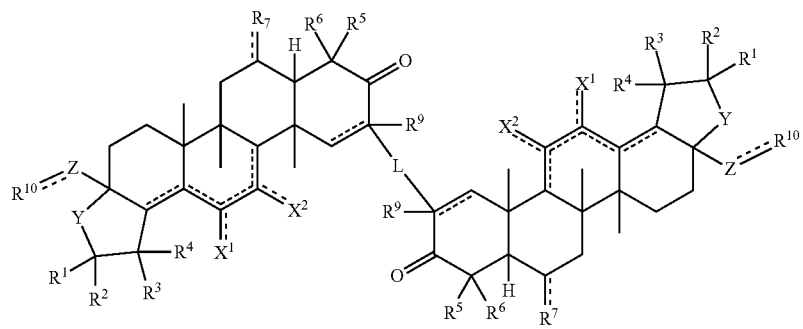

Formula IV wherein $X^1$, $X^2$, Y, Z, $R^1$, $R^2$, $R^3$, $R^4$, $R^5$, $R^6$, $R^7$, $R^9$ and $R^{10}$ are as defined for Formula III and L is —C≡C—R—C≡C—, —C(=O)—, —C≡C—, —C≡C—N(—R)—, —C(=O)—N(—R)—, —C≡C—C(=O)—, —Ar—C(=O)—, or —C≡C—C(=O)—Ar—, wherein R is hydrogen, or an alkyl, aryl, alkenyl, or alkynyl group. Exemplary dimers include compounds 10-17.

As used herein, "hydrogen" means —H; "hydroxyl" means —OH; "oxo" means =O; "halo" or "halogen" means independently —F, —Cl, —Br or —I; "hydroxyamino" means —NHOH; "nitro" means —NO$_2$; "cyano" means —CN; "azido" means —N$_3$; "mercapto" means —SH; "thio" means =S; "sulfonyl" means —S(O)$_2$— (see additional definitions of groups containing the term sulfonyl, e.g., alkylsulfonyl); and "silyl" means —SiH$_3$ (see additional definitions of group(s) containing the term silyl, e.g., alkylsilyl).

For the groups below, the following parenthetical subscripts further define the groups as follows: "(Cn)" defines the exact number (n) of carbon atoms in the group. For example, "$C_1$-$C_{15}$-alkoxy" designates those alkoxy groups having from 1 to 15 carbon atoms (e.g., 1, 2, 3, 4, 5, 6, 7, 8, 9, 10, etc. or any range derivable therein (e.g., 3-10 carbon atoms)).

The term "alkyl" refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$, —CH$_2$CH$_3$, —CH$_2$CH$_2$CH$_3$, —CH(CH$_3$)$_2$, —CH(CH$_2$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$C(CH$_3$)$_3$, cyclobutyl, cyclopentyl, cyclohexyl, and cyclohexylmethyl are non-limiting examples of alkyl groups.

The term "alkanediyl" refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups.

The term "alkenyl" refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$, —CH=CHCH$_3$, —CH=CHCH$_2$CH$_3$, —CH$_2$CH=CH$_2$, —CH$_2$CH=CHCH$_3$, and —CH=CH—C$_6$H$_5$.

The term "alkenediyl" refers to a nonaromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$— are non-limiting examples of alkenediyl groups.

The term "alkynyl" refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups.

The term "alkynediyl" refers to a nonaromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups.

The term "aryl" refers to a monovalent group with an aromatic carbon atom as the point of attachment, said carbon atom forming part of a six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, -ethylphenyl, propylphenyl, —C$_6$H$_4$CH(CH$_3$)$_2$, —C$_6$H$_4$CH(CH$_2$)$_2$, methylethylphenyl, vinylphenyl, naphthyl, and the monovalent group derived from biphenyl.

The term "arenediyl" refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group is composed of carbon and hydrogen. Non-limiting examples of arenediyl groups include:

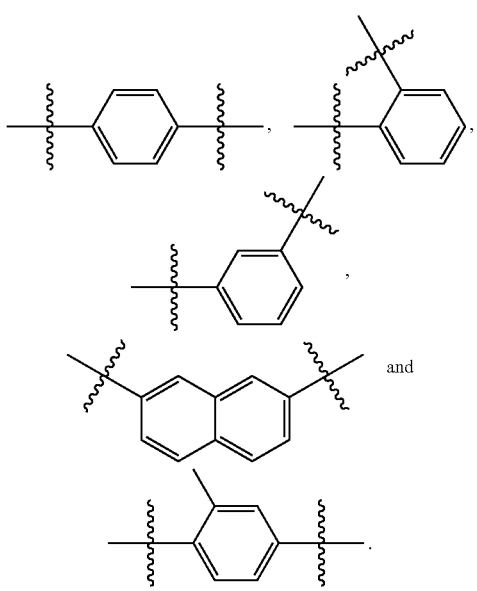

The term "aralkyl" refers to the monovalent group -alkanediyl-aryl, in which the terms alkanediyl and aryl are each used in a manner consistent with the definitions provided above. Non-limiting examples of aralkyls include 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms.

The term "heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms).

The term "heteroaralkyl" refers to the monovalent group -alkanediyl-heteroaryl, in which the terms alkanediyl and heteroaryl are each used in a manner consistent with the definitions provided above. Non-limiting examples of aralkyls include pyridylmethyl, and thienylmethyl.

The term "acyl" refers to a monovalent group with a carbon atom of a carbonyl group as the point of attachment, further having a linear or branched, cyclo, cyclic or acyclic structure. The groups, —CHO, —C(=O)CH$_3$, —C(=O)CH$_2$CH$_3$, —C(=O)CH$_2$CH$_2$CH$_3$, —C(=O)CH(CH$_3$)$_2$, —C(=O)CH(CH$_2$)$_2$, —C(=O)C$_6$H$_5$, —C(=O)C$_6$H$_4$CH$_3$, and —C(=O)C$_6$H$_4$CH$_2$CH$_3$ are non-limiting examples of acyl groups. The term "acyl" therefore encompasses, but is not limited to groups sometimes referred to as "alkyl carbonyl" and "aryl carbonyl" groups.

The term "alkoxy" refers to the group —OR, in which R is an alkyl, as that term is defined herein. Non-limiting examples of alkoxy groups include —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl.

Similarly, the terms "alkynyloxy," "alkynyloxy," "aryloxy," "aralkoxy," "heteroaryloxy," "heteroaralkoxy" and "acyloxy," refer to groups, defined as —OR, in which R is alkenyl, alkynyl, aryl, aralkyl, heteroaryl, heteroaralkyl and acyl, respectively, as those terms are defined above.

The term "alkoxydiyl" refers to a non-aromatic divalent group, wherein the alkoxydiyl group is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds in the group's backbone, further having no backbone atoms other than carbon or oxygen and having at least one of each of these atoms in the group's backbone. The groups, —O—CH$_2$CH$_2$—, —CH$_2$—O—CH$_2$CH$_2$—, —O—CH$_2$CH$_2$—O— and —O—CH$_2$—O— are non-limiting examples of alkoxydiyl groups.

The term "alkenyloxydiyl" refers to a divalent group that is nonaromatic prior to attachment, wherein the alkenyloxydiyl group is attached with two σ-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment, further having no backbone atoms other than carbon or oxygen and having at least one of each of these atoms in the group's backbone. The groups, —O—CH=CH—, —O—CH=CHO— and —O—CH=CHCH$_2$— are non-limiting examples of alkenyloxydiyl groups.

The term "amino" refers to a moiety of the formula —NRR', wherein R and R' are independently hydrogen, alkyl, cycloalkyl, heterocycloalkyl, aryl or heteroaryl.

The term "alkylamino" refers to the group —NHR, in which R is an alkyl, as that term is defined above. Non-limiting examples of alkylamino groups include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl.

Similarly, the terms "alkoxyamino," "alkenylamino," "alkynylamino," "arylamino," "aralkylamino," "heteroarylamino," "heteroaralkylamino," and "alkylsulfonylamino" refer to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$.

The term "dialkylamino" refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include —NHC(CH$_3$)$_3$, —N(CH$_3$)CH$_2$CH$_3$, —N(CH$_2$CH$_3$)$_2$, N-pyrrolidinyl, and N-piperidinyl.

The term "alkylaminodiyl" refers to a non-aromatic divalent group, wherein the alkylaminodiyl group is attached with two σ-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no double or triple bonds in the group's backbone, further having no backbone atoms other than carbon or nitrogen and having at least one of each of these atoms in the group's backbone. The groups, —NH—$CH_2CH_2$—, —$CH_2$—NH—$CH_2CH_2$—, —NH—$CH_2CH_2$—NH— and —NH—$CH_2$—NH— are non-limiting examples of alkylaminodiyl groups.

The term "alkenylaminodiyl" refers to a divalent group that is nonaromatic prior to attachment, wherein the alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon-nitrogen double that is non-aromatic at least prior to attachment, further having no backbone atoms other than carbon or nitrogen. The groups —NH—CH=CH—, —NH—CH=N— and —NH—CH=CH—NH— are non-limiting examples of alkenylaminodiyl groups.

The term "alkenylaminooxydiyl" refers to a divalent group, wherein the alkenylaminooxydiyl group is attached with two σ-bonds, which may become aromatic upon attachment, with two atoms selected from the group consisting of carbon, oxygen and nitrogen as points of attachment, further having a linear or branched, cyclo, cyclic or acyclic structure, at least one carbon-carbon double bond, carbon-nitrogen double, or nitrogen-nitrogen double bond that is non-aromatic at least prior to attachment, further having no backbone atoms other than carbon nitrogen or oxygen and having at least one of each of these three atoms in the backbone. The group —O—CH=N—, is a non-limiting example of an alkenylaminooxydiyl group.

The term "amido" (acylamino) refers to the group —NHR, in which R is acyl, as that term is defined herein. A non-limiting example of an acylamino group is —NHC(=O)$CH_3$.

The term "alkylthio" refers to the group —SR, in which R is an alkyl, as that term is defined above. Non-limiting examples of alkylthio groups include —$SCH_3$, —$SCH_2CH_3$, —$SCH_2CH_2CH_3$, —$SCH(CH_3)_2$, —$SCH(CH_2)_2$, —S-cyclopentyl, and —S-cyclohexyl.

Similarly, the terms "alkenylthio," "alkynylthio," "arylthio," "aralkylthio," "heteroarylthio," "heteroaralkylthio" and "acylthio" refer to groups, defined as —SR, in which R is alkenyl, alkynyl, aryl, aralkyl, heteroaryl, heteroaralkyl and acyl, respectively, as those terms are defined above.

The term "thioacyl" refers to a monovalent group with a carbon atom of a thiocarbonyl group as the point of attachment, further having a linear or branched, cyclo, cyclic or acyclic structure. The groups —CHS, —C(=S)$CH_3$, —C(=S)$CH_2CH_3$, —C(=S)$CH_2CH_2CH_3$, —C(=S)CH$(CH_3)_2$, —C(=S)CH$(CH_2)_2$, —C(=S)$C_6H_5$, —C(=S)$C_6H_4CH_3$, —C(=S)$C_6H_4CH_2CH_3$, —C(=S)$C_6H_3(CH_3)_2$, and —C(=S)$CH_2C_6H_5$, are non-limiting examples of thioacyl groups. The term "thioacyl" therefore encompasses, but is not limited to, groups sometimes referred to as "alkyl thiocarbonyl" and "aryl thiocarbonyl" groups.

The term "alkylsulfonyl" refers to the group —S(=O)$_2$R, in which R is an alkyl, as that term is defined above. Non-limiting examples of alkylsulfonyl groups include: —S(=O)$_2$CH$_3$, —S(=O)$_2$CH$_2$CH$_3$, —S(=O)$_2$CH$_2$CH$_2$CH$_3$, —S(=O)$_2$CH(CH$_3$)$_2$, —S(=O)$_2$CH(CH$_2$)$_2$, —S(=O)$_2$-cyclopentyl, and —S(=O)$_2$-cyclohexyl.

Similarly, the terms "alkenylsulfonyl," "alkynylsulfonyl," "arylsulfonyl," "aralkylsulfonyl," "heteroarylsulfonyl," and "heteroaralkylsulfonyl" refer to groups, defined as —S(O)$_2$R, in which R is alkenyl, alkynyl, aryl, aralkyl, heteroaryl, and heteroaralkyl, respectively, as those terms are defined above.

The term "alkylsulfinyl" refers to the group —S(=O)R, in which R is an alkyl, as that term is defined above. Non-limiting examples of alkylsulfinyl groups include —S(=O)$CH_3$, —S(=O)$CH_2CH_3$, —S(=O)$CH_2CH_2CH_3$, —S(=O)CH$(CH_3)_2$, —S(=O)CH$(CH_2)_2$, —S(=O)-cyclopentyl, and —S(=O)-cyclohexyl.

Similarly, the terms "alkynylsulfinyl," "alkynylsulfinyl," "arylsulfinyl," "aralkylsulfinyl," "heteroarylsulfinyl" and "heteroaralkylsulfinyl" refer to groups, defined as —S(=O)R, in which R is alkenyl, alkynyl, aryl, aralkyl, heteroaryl, and heteroaralkyl, respectively, as those terms are defined above.

The term "alkylammonium" refers to a group, defined as —$NH_2R^+$, —$NHRR'^+$, or —$NRR'R''^+$, in which R, R' and R" are the same or different alkyl groups, or any combination of two of R, R' and R" can be taken together to represent an alkanediyl. Non-limiting examples of alkylammonium cation groups include —$NH_2(CH_3)^+$, —$NH_2(CH_2CH_3)+$, —$NH_2(CH_2CH_2CH_3)+$, —$NH(CH_3)_2^+$, —$NH(CH_2CH_3)_2^+$, —$NH(CH_2CH_2CH_3)_2^+$, —$N(CH_3)_3^+$, —$N(CH_3)(CH_2CH_3)_2^+$, —$N(CH_3)_2(CH_2CH_3)^+$, —$NH_2C(CH_3)_3^+$, —$NH(cyclopentyl)_2^+$, and —$NH_2(cyclohexyl)^+$.

The term "alkylsulfonium" refers to the group —SRR', in which R and R' can be the same or different alkyl groups, or R and R' can be taken together to represent an alkanediyl. Non-limiting examples of alkylsulfonium groups include —$SH(CH_3)$, —$SH(CH_2CH_3)$, —$SH(CH_2CH_2CH_3)$, —$S(CH_3)_2$, —$S(CH_2CH_3)_2$, —$S(CH_2CH_2CH_3)_2$, —SH(cyclopentyl), and —SH(cyclohexyl).

The term "alkylsilyl" refers to a monovalent group, defined as —$SiH_2R$, —SiHRR', or —SiRR'R", in which R, R' and R" can be the same or different alkyl groups, or any combination of two of R, R' and R" can be taken together to represent an alkanediyl. The groups —$SiH_2CH_3$, —$SiH(CH_3)_2$, —$Si(CH_3)_3$ and —$Si(CH_3)_2C(CH_3)_3$, are non-limiting examples of unsubstituted alkylsilyl groups.

The term "alkylphosphonyl" refers to the group —OPO(OR)$_2$, where R is alkyl, as defined herein.

The term "alkylphosphate" refers to the group —OP(=O)(OH)(OR), in which R is an alkyl, as that term is defined above. Non-limiting examples of alkylphosphate groups include —OP(=O)(OH)(OMe) and —OP(=O)(OH)(OEt).

The term "dialkylphosphate" refers to the group —OP(=O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include —OP(=O)(OMe)$_2$, —OP(=O)(OEt)(OMe) and —OP(=O)(OEt)$_2$.

"Cycloalkyl" means a non-aromatic mono- or multicyclic ring system including about 3 to about 10 carbon atoms, preferably about 5 to about 10 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclyl" or "heterocycloalkyl" means a non-aromatic saturated monocyclic or multicyclic ring system including about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like.

Any of the groups described herein may be unsubstituted or optionally substituted. When modifying a particular group, "substituted" means that the group the term modifies may, but does not have to, be substituted. Substitutions typically replace an available hydrogen with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

A triterpenoid compound of this invention may be used in vivo or in vitro and be provided in a pharmaceutical composition. A triterpenoid compound of this invention finds application in modulating IFN-γ-induced NO production in macrophages. Alternatively, the triterpenoid compound is of use in modulating excessive nitric oxide or prostaglandin formation in a subject.

In a further embodiment, the triterpenoid compounds of the invention are of use in preventing or treating a disorder characterized by overexpression of iNOS or COX-2 genes, e.g., cancer, diabetic nephropathy, neurodegenerative disease, rheumatoid arthritis, inflammatory bowel disease, and other diseases whose pathogenesis is believed to involve excessive production of either nitric oxide or prostaglandins. In a particular embodiment, the neurodegenerative disease includes Parkinson's disease, Alzheimer's disease, multiple sclerosis, and amyotrophic lateral sclerosis. The cancer may include, e.g., a leukemic cancer or a solid cancer. A leukemic cancer is a cancer of a blood cell, a myeloid cell, a monocytic cell, a myelocytic cell, a promyelocytic cell, a myeloblastic cell, a lymphocytic cell, or a lymphoblastic cell. A solid cancer is a cancer of a bladder cell, a breast cell, a lung cell, a colon cell, a prostate cell, a liver cell, a pancreatic cell, a stomach cell, a testicular cell, a brain cell, an ovarian cell, a skin cell, a brain cell, a bone cell, or a soft tissue cell.

Moreover, the invention provides use of the compounds synthesized herein in the treatment and prevention of graft versus host disease (GVHD) by providing a triterpenoid compound of the invention either alone or in conjunction with another agent, such as an immunosuppressive agent such as a corticosteroid or tacrolimus, or a chemotherapeutic agent for the treatment of GVHD. In graft versus host disease the donor immune system mounts a response against the host's organs or tissue. As CDDO compounds, either alone or in conjunction with other agents, can induce apoptosis by inhibiting Bcl-2 and have activity in lymphoid tissue, it is contemplated that the instant triterpenoid compounds can be used to provide therapy for graft versus host diseases.

The invention is described in greater detail by the following non-limiting examples.

Example 1

Synthesis of CDDO-Me from Oleanolic Acid

As shown in Scheme 4, the natural triterpenoid oleanolic acid (1) was used as the starting material in the synthesis of CDDO-Me. The improved method commences with methylation of the carboxylic acid of oleanolic acid (1) to afford methyl ester 2 in quantitative yield. With ester 2, activation of the A-ring is fulfilled by 2-iodoxybenzoic acid-mediated twofold oxidation to give enone 3. Epoxidation with meta-chloroperoxybenzoic acid, followed by direct C-ring enolization and A-ring enone bromination with bromine and hydrobromic acid, affords key intermediate 4. With bromide 4 in hand, a cross-coupling reaction with copper cyanide provides CDDO-Me (5) in only five steps (four operations) from oleanolic acid (Scheme 4). This is an improvement over conventional methods, which require 10 steps. Moreover, intermediate 4 was prepared in high yield and few overall steps, thereby providing a base compound for development of additional analogs and derivatives.

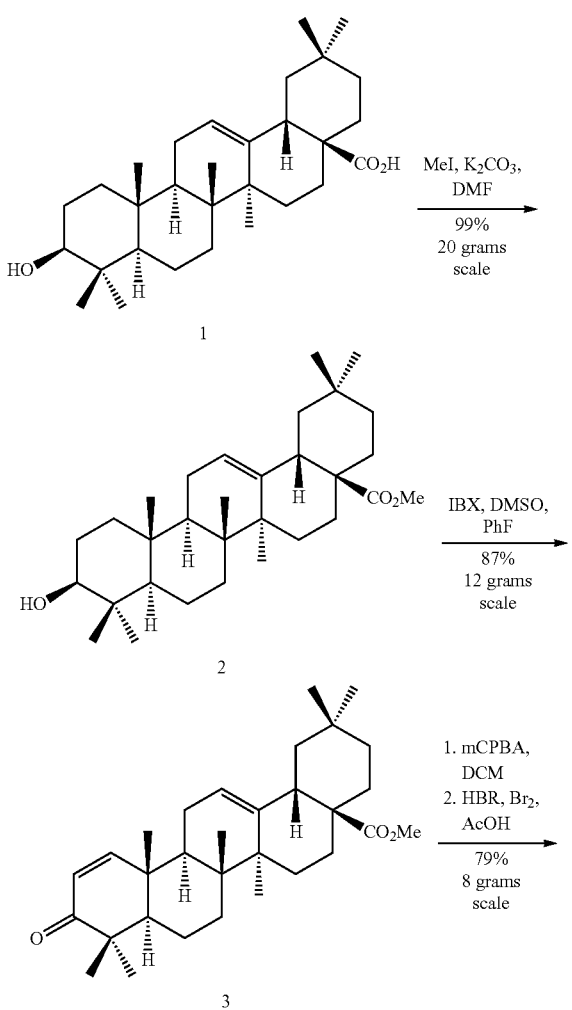

SCHEME 4

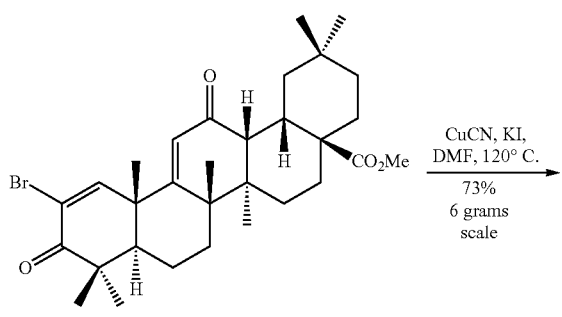

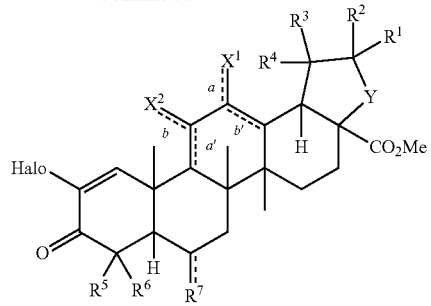

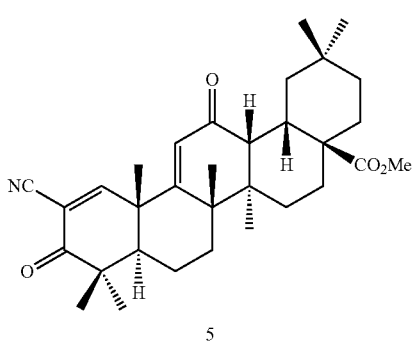

Unless otherwise specified, the reagents used in the instant methods are conventionally known in the art. For example, MeI refers to methyl iodide, DMF refers to dimethylformamide, IBX is 2-iodoxybenzoic acid, DMSO is dimethyl sulfoxide, PhF is phenyl fluoride, mCPBA refers to meta-chloroperoxybenzoic acid, HBr is hydrogen bromide, DCM is dichloromethane, AcOH is acetic acid, and CuCN is copper cyanide.

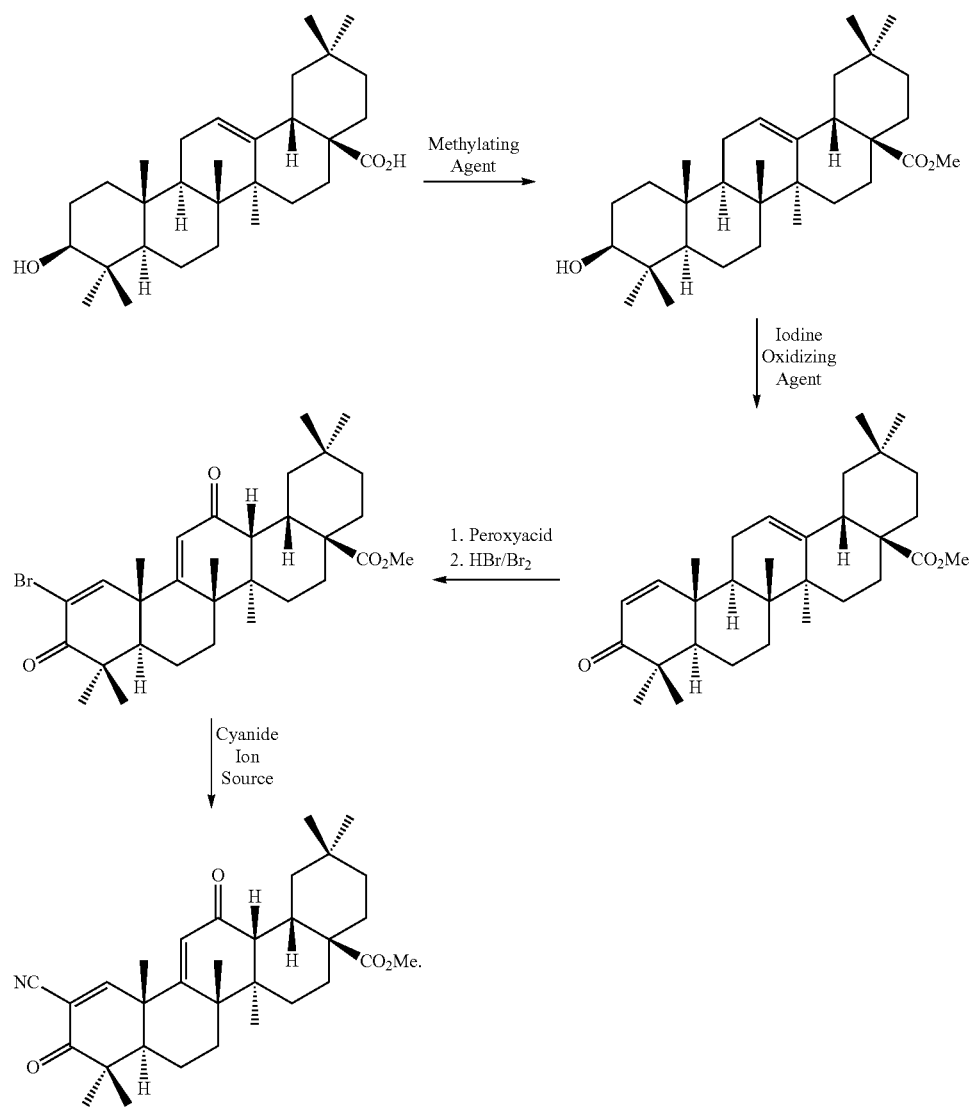

What is claimed is:

1. A method for preparing a triterpenoid compound comprising:
   (a) methylating the carboxylic acid group of a compound of Formula I to afford a methyl ester;
   (b) oxidizing the hydroxyl group of the methyl ester and forming a double bond in Ring A to form an enone;
   (c) epoxidating Ring C of the enone to form an epoxide; and
   (d) forming a C-ring enol and halogenating the A-ring enone to yield a compound of Formula II

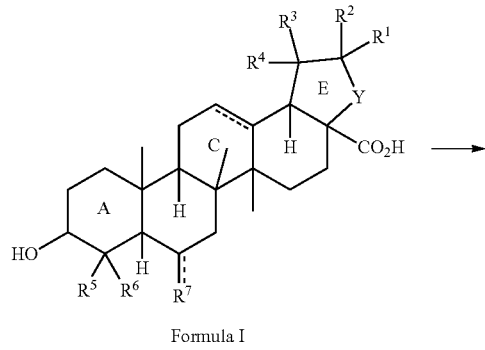

Formula I

Formula II wherein
   $X^1$ is oxygen, dashed bonds a and a' are present, $X^2$ is hydrogen and dashed bonds b and b' are absent, or
   X is oxygen, dashed bonds b and b' are present, $X^1$ is hydrogen and dashed bonds a and a' are absent;
   Y is —$CH_2$— or —$CH_2$—$CH_2$—;
   $R^1$, $R^2$, $R^3$ and $R^4$ are each independently a hydrogen, hydroxyl, alkyl, substituted alkyl, alkenyl, alkoxy or substituted alkoxy group;
   $R^5$ and $R^6$ are each independently hydrogen, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, hetero-arylamino, heteroaralkylamino, amido, or a substituted version of any of these groups, or
   $R^5$ and $R^6$ are taken together and are alkanediyl, alkenediyl, arenediyl, alkoxydiyl, alkenyloxydiyl, alkylaminodiyl, alkenylaminodiyl, or alkenylaminooxydiyl; and
   $R^7$ is hydrogen, hydroxy or oxo.

2. The method of claim 1, wherein the compound of Formula I is oleanolic acid, ursolic acid, betulinic acid, sumaresinolic acid or hederagenin.

3. The method of claim 1, wherein step (a) comprises an electrophilic methyl source.

4. The method of claim 1, wherein step (b) comprises an iodine oxidizing agent.

5. The method of claim 1, wherein step (c) comprises a peroxyacid.

6. The method of claim 1, wherein step (d) comprises a hydrogen halide and diatomic halogen molecule.

7. The method of claim 1, further comprising the step of contacting a compound of Formula II with a cyanide ion source.

8. The method of claim 1, further comprising aminating the compound of Formula II.

9. The method of claim 8, wherein amination comprises a Buchwald-Hartwig amination reaction.

10. The method of claim 1, further comprising coupling or cross-coupling an alkyl, alkenyl, alkynyl or aryl group to a compound of Formula II.

11. The method of claim 10, wherein said coupling or cross-coupling comprises a Sonogashira, Suzuki, Stille, or Negishi reaction.

12. A method for preparing 2-cyano-3,12-dioxoolean-1,9(11)-dien-28-oic acid methyl ester (CDDO-Me), wherein said method comprises the following series of reactions